United States Patent
Choi et al.

(10) Patent No.: US 8,544,316 B2
(45) Date of Patent: Oct. 1, 2013

(54) MICRO VISCOMETER

(75) Inventors: Sungjoon Choi, Daegu (KR); Daeyoung Shin, Incheon (KR); Kangwon Lee, Cheonan-si (KR)

(73) Assignee: Korea Institute of Industrial Technology, Cheonan (KR)

( * ) Notice: Subject to any disclaimer, the term of this patent is extended or adjusted under 35 U.S.C. 154(b) by 288 days.

(21) Appl. No.: 13/184,709

(22) Filed: Jul. 18, 2011

(65) Prior Publication Data

US 2013/0019661 A1  Jan. 24, 2013

(51) Int. Cl.
*G01N 11/10*  (2006.01)

(52) U.S. Cl.
USPC ........................................... 73/54.41

(58) Field of Classification Search
USPC ........................................... 72/54.41
See application file for complete search history.

(56) References Cited

U.S. PATENT DOCUMENTS

| | | | |
|---|---|---|---|
| 3,882,732 A * | 5/1975 | Fletcher et al. ............... | 181/0.5 |
| 5,257,529 A | 11/1993 | Taniguchi et al. | |
| 6,141,625 A | 10/2000 | Smith et al. | |
| 6,322,624 B1 | 11/2001 | Titterington et al. | |
| 6,402,703 B1 | 6/2002 | Kensey et al. | |
| 6,428,488 B1 | 8/2002 | Kensey et al. | |
| 6,571,608 B2 | 6/2003 | Shin et al. | |
| 6,624,435 B2 | 9/2003 | Kensey et al. | |
| 6,732,573 B2 | 5/2004 | Shin et al. | |
| 2005/0183496 A1 | 8/2005 | Baek | |
| 2008/0134765 A1 | 6/2008 | Baek | |
| 2008/0289400 A1 | 11/2008 | Quist | |

FOREIGN PATENT DOCUMENTS

| | | |
|---|---|---|
| EP | 1814170 A3 | 8/2007 |
| KR | 10-0741262 B1 | 7/2007 |

OTHER PUBLICATIONS

Sungjoon Choi, Wonkyu Moon and Geunbae Lim, "A micro-machined viscosity-variation monitoring device using propagation of acoustic waves in microchannels," Journal of Micromechanics and Microengineering, 20 (2010).

* cited by examiner

*Primary Examiner* — Peter Macchiarolo
*Assistant Examiner* — Alex Devito
(74) *Attorney, Agent, or Firm* — Patent Office of Dr. Chung S. Park

(57) ABSTRACT

Disclosed is a micro viscometer comprising a first chamber and a second chamber positioned with an interval; a micro channel that connects the first chamber and the second chamber; and a first thin film and a second thin film arranged on top of the first chamber and the second chamber, respectively, wherein a height of the first chamber and second chamber are substantially identical to a half wavelength corresponding a first resonant frequency of the first thin film and the second thin film, respectively, and a width of the first chamber and the second chamber are narrower than the height of the first chamber and the second chamber.

12 Claims, 10 Drawing Sheets

(a)

(b)

MICRO VISCOMETER

TECHNICAL FIELD

This present application relates generally to a Micro Viscometer, a device for measuring the viscosity of fluids.

BACKGROUND ART

Generally, viscosity is a coefficient that expresses the physical property of the fluid viscosity volume, and various types of viscometers are developed and used to measure this type of viscosity.

A viscometer called the Greenspan viscometer (Refer to M. Greenspan and F. N. Wimenitz, "An Acoustic Viscometer for Gases-I," NBS Report 2658 (1953)), which was invented in 1953 by Greenspan and Wimenitz to measure the viscosity of gas with a design that comprises of two Helmholtz Resonators that are attached and face each other, exists, however, this viscometer relatively takes up much space and the performance shows a 38% error margin that was considered not to be suitable structure.

In 1996, K. A. Gillis came up with a more precise viscometer, compared to the Greenspan viscometer, by going through an experimental error and correction process to reduce the errors within the range of ±0.5% and derive more accurate gas viscosity measurements. (Refer to R. A. Aziz, A. R. Janzen, and M. R. Moldover, Phys. Rev. Lett. 74, 1586 (1995))

However, issues for this method existed, where the valid frequency section for this method was limited only to the low frequency domain. For example, the viscometer designed by K. A. Gillis could only be applied to low frequency under 200 Hz. The reason for this phenomenon was because the Helmholtz Resonator was applied assuming that the product of the wave number of the sound wave and the characteristic length was greatly smaller than 1. Furthermore, due to the fact that no measurements were made for liquids, the measurements were restricted to gas and the size was large that required a mass amount of fluid.

Also, U.S. Pat. No. 6,141,625 discloses a viscosity module with a crystal resonant sensor, where this module relates to a mobile viscometer that can measure the viscosity of the fluid even with a small quantity of reagent. This viscometer utilizes a disk type thin crystal film for the viscosity sensor.

To obtain this type of crystal resonant frequency, the sensor operates in thickness shear mode by positioning electrodes on the top and bottom portion of the thin film and passing a signal. If a certain liquid exists on the top surface of the crystal, then power loss occurs that cause damping in the crystal resonant frequency. Eventually, the viscosity of the liquid can be measured by checking the value of damping.

However, accurate measurements are only obtainable when a viscosity module with a crystal resonant sensor is placed horizontally, liquid is equally distributed and a large amount of liquid. In other words, the viscosity module with a crystal resonant sensor needs several ml of liquid with assuming that the volume of a single water drop is 0.04 ml and an issue exists where it is impossible to take measurements with the volume of a single water drop. Furthermore, this type of viscometer has demerits that it is impossible to make measurements of gas, since it utilizes the gravity applied on liquids.

On the other hand, many forms exist for viscometers that use the capillary tube, however, most viscometers utilize the differential head caused from gravity as it is disclosed in U.S. Pat. Nos. 6,322,624, 6,402,703, 6,428,488, 6,571,608, 6,624, 435, 6,732,573, and 5,257,529, etc. Due to the reason that the viscometer uses the differential head, measurements are limited to liquids, furthermore, issues in the amount of liquids needs exist even if capillary tubes, where the volume of liquids necessary is more than a couple dozen to hundreds of id that is regarded to be a large amount.

SUMMARY

A first embodiment of the present invention regarding the viscometer provides an article comprising a first chamber and a second chamber positioned with an interval; a micro channel that connects the first chamber and the second chamber; and a first thin film and a second thin film arranged on the first chamber and the second chamber, respectively, wherein a height of the first chamber and second chamber are substantially identical to a half wavelength corresponding a first resonant frequency of the first thin film and the second thin film, respectively, and a width of the first chamber and the second chamber are narrower than the height of the first chamber and the second chamber, respectively.

The resonant frequency of the first thin film may be identical to the resonant frequency of the second thin film.

The first thin film and the second thin film each may includes a silicon wafer and an insulator deposited on a top and a bottom surface of the silicon wafer.

The insulator comprises Si type layer.

At least one side of the first chamber, the second chamber and the micro channel may be coated with hydrophilic layer.

A volume value of the first chamber may be substantially identical to that of the second chamber.

A second embodiment of the present invention regarding the viscometer provides an article comprising a first chamber and a second chamber positioned with an interval; a micro channel that connects the first chamber and the second chamber; and a first thin film and a second thin film arranged on top of the first chamber and the second chamber, respectively, wherein a height of the first chamber and second chamber are substantially identical to a wavelength corresponding a second resonant frequency of the first thin film and the second thin film, respectively, and a width of the first chamber and the second chamber are narrower than a half wavelength corresponding a second resonant frequency of the first thin film and the second thin film.

DETAILED DESCRIPTION

Figure 1:
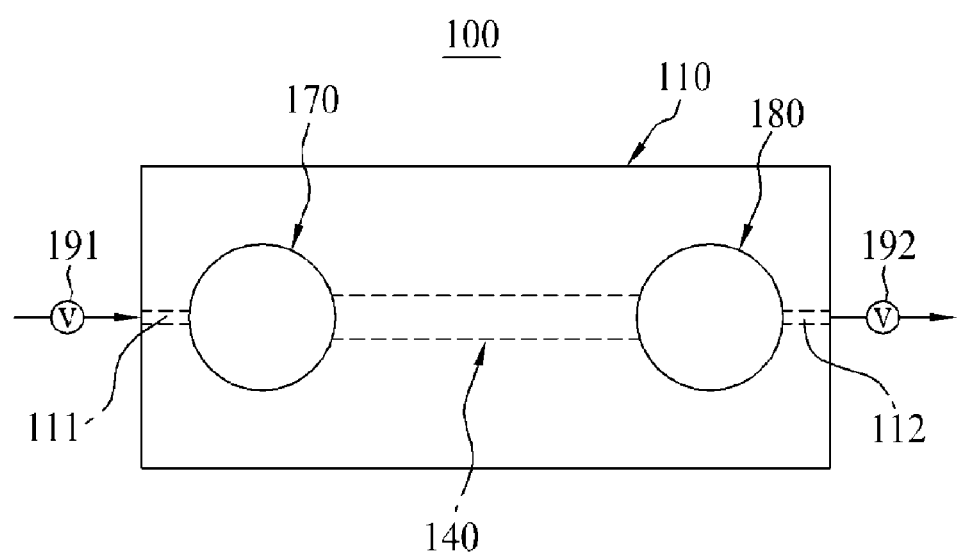
FIG. 1 is a cross-sectional view in accordance with the first embodiment of the present invention illustrating a micro viscometer.
Figure 2:
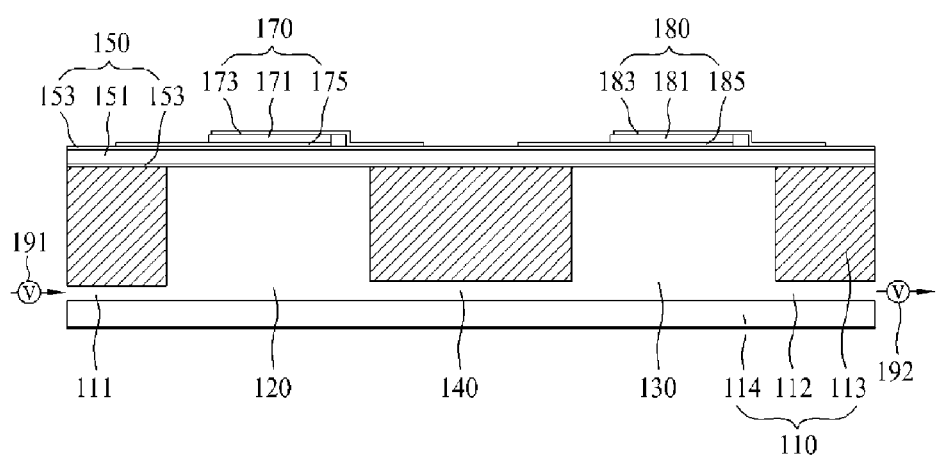
FIG. 2 is an end view of the first embodiment of the present invention illustrating a micro viscometer.

FIG. 1 is a cross-sectional view in accordance with the first embodiment of the present invention illustrating a micro viscometer and FIG. 2 is an end view of the first embodiment of the present invention illustrating a micro viscometer.

As illustrated, a micro viscometer 100 positions 2 Helmholtz resonators in parallel so that viscosity can be measured even with a small amount of fluid. The micro viscometer comprises substrate a thin film 150, an actuating part 170 and a sensing part 180, a body 110 that includes a substrate 113 and a cover 114.

The substrate 113 and the cover 114 are bonded onto the body 110 with an interval to provide space for an inlet 111, an outlet 112, a first chamber 120, a second chamber 130 and a micro channel 140.

The substrate 113 can be composed of a Silicon On Insulator (SOI) that possess a Silicon single crystal layer on top of the silicon wafer or insulator, and space for the first chamber 120 and the second chamber 130 prepared through the Deep Reactive Ion Etching (DRIE) process is provided one side of the substrate 113.

Anodic bonding is operated on the cover 114 and the substrate 113 so that decay space is given to the inlet 111, the first chamber 120, the second chamber 130, the outlet 112 and the micro channel 140. Also, a material of the cover 114 may be transparent material such as a glass to visually confirm a fluid within the cover 114.

On one side of the inlet 111 and the outlet 112 of the body 110, open-close valves 191, 192 are provided so that fluids inputted within the body 110 does not flow outside. To open-close the fluid movement, open-close valves 191, 192 may be omitted according to a method of measuring the viscosity of the fluid.

The first chamber 120 and the second chamber 130 of the body 110 are connected to the inlet 111 and outlet 112, respectively. It is desired for the first chamber 120 and the second chamber 130 to have substantially identical volume and height. The design is to minimize an error that may occur from the vibration applied on the thin film 150 when measuring the viscosity of the fluid.

The micro channel 140 connects the first chamber 120 with the second chamber 130 and provides space for viscosity loss of the fluid when measuring the fluid viscosity within the body.

The thin film 150 is positioned on the substrate 113 to cover the first chamber 120 and second chamber 130. The thin film 150 separates the first chamber 120 and the second chamber 130 from the outside and, during operation, vibrates with the filled fluids within the first chamber 120 and the second chamber 130. This type of thin film 150 is formed in a single film, as illustrated, however, it can have additional two thin films for the first chamber 120 and the second chamber 130, correspondingly.

Furthermore, the thin film 150 is formed with Silicon Nitride (SiN) laminated onto the Silicon wafer, and comprises an insulator 153 attached to the top and bottom of the silicon wafer 151 as illustrated.

It is suitable to use a Si type insulator such as Silica dioxide ($SiO_2$) as the insulator 153.

The actuating part 170 locates on the thin film 150 that corresponds to the first chamber 120 and conducts vibration onto the thin film 150 so that the vibration can transfer to the fluid within the first chamber 120. For the convenience of explanation, the portion of the thin film 150 that corresponds to the first chamber 120 is called the first thin film.

The actuating part 170 comprises a first electrode 175, a piezoelectric layer 171 arranged on the first electrode 175 and a second electrode 173 that is positioned on the piezoelectric layer 171. One side of the second electrode 173 is separated from the first electrode 175 and connected to the first thin film, while the other side of the second electrode 173 is located on the first piezoelectric layer 171.

The sensing part 180 comprises the thin film 150 that corresponds to the second chamber 130 and senses the vibration or the pressure of the fluid within the second chamber 130 that is transferred to the thin film 150. For the convenience of explanation, the portion of the thin film 150 that corresponds to the second chamber 130 is called the second thin film.

This type of sensing part 180, similar to the actuating part 170, comprises a third electrode 185 disposed on the second thin film and a second piezoelectric layer 181 arranged on top of the third electrode 185 and a fourth electrode 183 positioned on the second piezoelectric layer 181. Thus, one side of the fourth electrode 183 is separated from the third electrode 185 and connected to the second thin film, while the other side of the fourth electrode 183 is arranged on one side of the second piezoelectric layer 181.

Meanwhile, the actuating part 170 and the sensing part 180 for example have used the piezoelectric layer for piezoelectric effects, however, it is not limited to this example and polymer materials with piezoelectric characteristic can also be utilized.

During operation, fluid, such as air, within the body 110 outflows through the outlet 112 to the outside, the inside pressure decreases and the fluid inflows within the body 110 through the inlet 111

It is suitable to have Hydrophilic surface treatment such as hydrophilic layer done on at least one side of the compositions within the body 110 of a micro viscometer 100 where it has contact with the fluid such as the inlet 111, outlet 112, first chamber 120, second chamber 130 and micro channel 140. This helps the inflow of the fluid within the body and prevents air bubble formation within the body that may occur from surface tension of the fluid.

On the other hand, open-close valves 191, 192 are shut off when the fluid fills the body 110 so that it can prevent the fluid to flow outside from the body 110 interior.

Next, by providing the voltage ($V_{input}$) as a Sine function similar to Equation 1 below in the frequency domain that includes resonant frequency of the system of a pair of first electrode 175 and second electrode 173 of the actuating part 170, the first piezoelectric layer 171 applies vibration to the first thin film.

$$V_{input} = V_0 \sin \omega t \qquad \text{Equation 1}$$

When the first thin film vibrates, a loss in sound wave occur due to the acoustic boundary layer inside the micro viscometer, or in other words the inside the body 110. This type of loss can be categorized into two; one is the loss($\alpha_v$) of the viscosity boundary layer($\delta_v$) within the micro channel that has the fastest particle velocity and the other is thermal loss ($\alpha_t$) that comes from the thermal boundary layer($\delta_t$) of the first chamber 120 and second chamber 130 that has large area to volume ratio.

When the viscosity boundary layer or the thermal boundary layer is greatly smaller than the radius or half the height, $r_c$, of the micro channel 140 this loss of the boundary layer has the relationship with the Q factor as shown in Equation 2.

$$\frac{1}{Q} = \frac{\alpha_v}{2\pi} + \frac{\alpha_t}{2\pi} = \frac{\delta_v}{r_c} + (\gamma - 1)\frac{\delta_t S}{\pi V} \qquad \text{Equation 2}$$

In this equation, the r is the ratio of specific heat of the fluid, s is the area of the chamber, v is the volume of the chamber, $\delta_v$ is the thickness of viscosity boundary layer of the micro channel 140 interior, $\delta_t$ is the thickness of thermal boundary layer of the chamber 120, 130.

The sound wave conveys to the second thin film possessing this loss and the frequency response outputted from the second thin film from the effects of the second piezoelectric layer 181 of the sensing part 180 can be measured.

When measuring the Q factor for this type of frequency response Equation 2 is used to measure the viscosity of fluid as shown in Equation 3.

$$v = \frac{\mu}{\rho} = \frac{\omega r_c^2}{2}\left\{\frac{1}{Q} + (1-\gamma)\frac{\delta_t S}{\pi V}\right\}^2 \qquad \text{Equation 3}$$

In this equation, v is the Kinematic Viscosity, $\mu$ is the Dynamic Viscosity and $\rho$ is the density.

Alternatively, a different method can be introduced, as discussed below, using a micro viscometer 100 according to one embodiment of the present invention, which is the Single-Frequency Driving Method (SFDM) that uses single frequency (or resonant frequency) to measure the viscosity.

For the method for measuring the viscosity from single frequency, a method for measuring the change or the viscosity of the fluid utilizing the frequency (or resonant frequency) instead of the Q factor is used to overcome onerous tasks of using sweeping on the frequency domain that applies the Q factor and finds the resonant frequency and directly obtains the half power band width, and also accurately deriving the Q factor due to the error of the resonant frequency or half power bandwidth.

Figure 3:
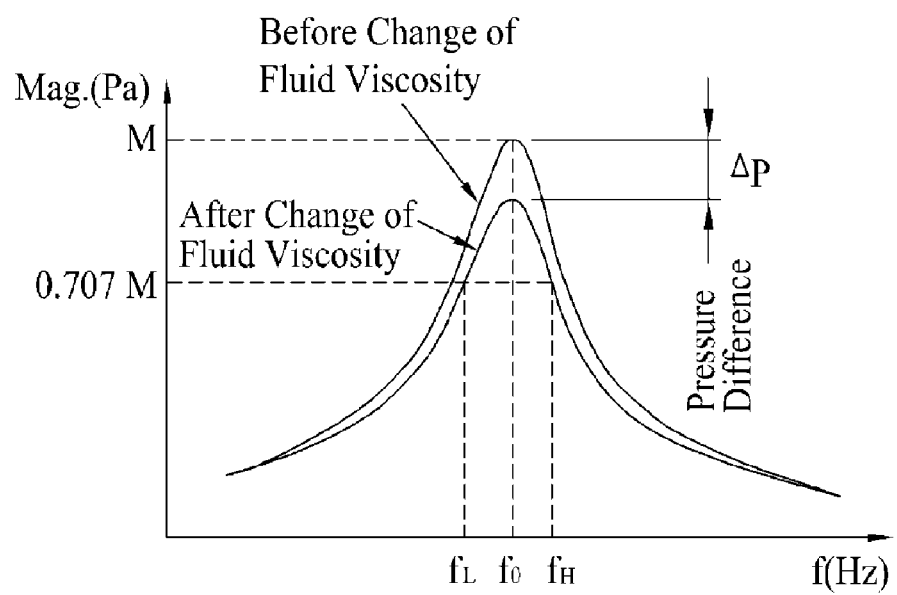
FIG. 3 is a graph used to explain the method of measuring the viscosity using resonant frequency from a micro viscometer, according to one embodiment of the present invention.

As illustrated in FIG. 3, the degree of acoustic pressure of the resonant frequency occurs as the fluid viscosity changes. By measuring the variance the change status of the viscosity can be measured and the desired fluid viscosity can be measured through compensation process.

Figure 4:
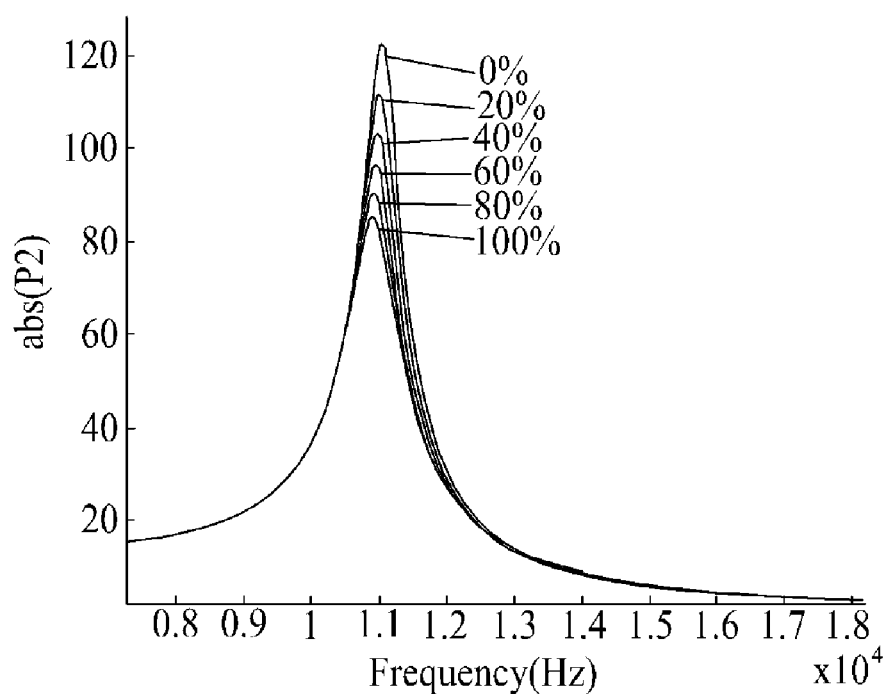
FIG. 4 is a graph used to explain the method of measuring the viscosity of the fluid using resonant frequency from a micro viscometer, according to one embodiment of the present invention.

Thus, fluid that serves as certain standards, for example water, measures the pressure sensed through the sensing part 180 according to the increase of frequency of the actuating part 170, and the viscosity of the this water saves data after measuring the pressure following frequency by stage that increase 20%, 40%, 60%, 80%, 100%, as illustrated in FIG. 4.

Afterwards, the pressure data sensed from the sensing part 180 compared to the frequency applied from the actuating part 170 on the fluid that needs measurement is obtained, and then the viscosity of the fluid that needs measurement is derived from the viscosity value that corresponds to the obtained data. The viscosity data that serves as a standard can be obtained more precisely than the interval of 20% as in one of the embodiments.

Also, the frequency $f_L$ and $f_H$ of the pressure (0.707M) is obtained, which becomes $1/\sqrt{2}$ of the maximum pressure (M) when the frequency alters between before and after the viscosity change of the fluid as illustrated in FIG. 3, then it is substituted into Equation 4 below to derive the Q factor. The viscosity of the fluid can be derived by using the Q factor, Equation 2 and Equation 3.

$$Q = \frac{f_o}{f_H - f_L} \qquad \text{Equation 4}$$

In another aspect, the Helmholtz resonator is usually applied in a couple dozen to a couple hundred Hz where the character size of the system is greatly shorter than the frequency wavelength, also expressed ka<<1. Here, the k is the wave number and a is a radius of the micro channel 140.

For this, one embodiment of the present invention uses MEMS process so that it holds a very small and thin type compared to general viscometers and resonant frequency increases up to hundreds of thousands to tens of millions Hz of the system itself.

Therefore, this present device expands and interprets the frequency domain so that is does not operate within the domain that does not satisfy the frequency domain of the Helmholtz resonator, which is ka<<1. For this purpose, the Total Acoustic Impedance of this invention expresses Equation 5, and using the equation as shown in Equation 6 where the reactance is 0 the resonant frequency can be derived.

$$Z_{ac} = Z_{mem1} + Z_{ca1} + 2Z_{end} + Z_{mc} + Z_{ca2} + Z_{mem2} \qquad \text{Equation 5}$$

Each value for the impedance is shown below.

$$Z_{mem1} = \frac{K_{ac}^{mem1}}{j\omega}$$

is the acoustic impedance of the first thin film 150, $$Z_{mem2} = \frac{K_{ac}^{mem2}}{j\omega}$$

is the acoustic impedance of the second thin film 160, $$Z_{ca1} = \frac{Z_0}{j\tan kh_1}\frac{1}{S_1}$$

is the acoustic impedance of the first chamber 120, $$Z_{ca2} = \frac{Z_0}{j\tan kh_2}\frac{1}{S_2}$$

is the acoustic impedance of the second chamber 120, $$Z_{mc} = j\frac{Z_0 \tan kl}{A}$$

is the acoustic impedance of the micro channel 140, $$Z_{end} = \frac{Z_0}{A}\{R_1(2kr_c) + jX_1(2kr_c)\}$$

is the acoustic impedance of the inlet 111 and outlet 112.

Furthermore, $K_{ac}^{mem1}$ and $K_{ac}^{mem2}$ are the Acoustic Stiffness of the first thin film 150 and second thin film 160 respectively, $h_1$ and $h_2$ correspondingly represents the height of the first chamber 120 and second chamber 130, and $$R_1(2kr_c) = 1 - \frac{2J_1(2kr_c)}{2kr_c} \quad (J_1: \text{Bessel function}),$$

$$X_1(2kr_c) = \frac{2H_1(2kr_c)}{2kr_c} \quad (H_1: \text{first order struve function})$$

are each represented from Acoustic Impedance $Z_{end}$.

If, the size and shape of the first chamber 120 and second chamber 130 are the same, $Z_{ac}$ can be more simply expressed, furthermore to find the resonant frequency by taking the reactance of $Z_{ac}$ can come up with Equation 6 as shown below.

$$Im(Z_{ac}) = \frac{2Z_0}{A}\left\{\frac{2}{2kr_c}\left[\frac{2}{\pi} - J_0(2kr_c) + \right.\right. \quad \text{Equation 6}$$
$$\left(\frac{16}{\pi} - 5\right)\frac{\sin(2kr_c)}{2kr_c} + \left(12 - \frac{36}{\pi}\right)\frac{1 - \cos(2kr_c)}{(2kr_c)^2}\right] +$$
$$\left.\frac{\tan kl}{2}\right\} - \left\{\frac{2Z_0}{\tan kh}\frac{1}{S} + \frac{2K_{ac}^{mem}}{\omega}\right\}$$

Therefore, frequency of the k value that satisfies $Im/(Z_{AC})=0$ corresponds to the resonant frequency. By substituting a variable x for these values, the follow Equation 7 can be derived.

$$k_n = x_x(n:\text{integer}) \quad \text{Equation 7}$$

Resonant frequency can be derived by using Equation 8 below.

$$f_1 = \frac{k_1 c_o}{2\pi} = \frac{x_1 c_o}{2\pi} \quad \text{Equation 8}$$

Figure 5:
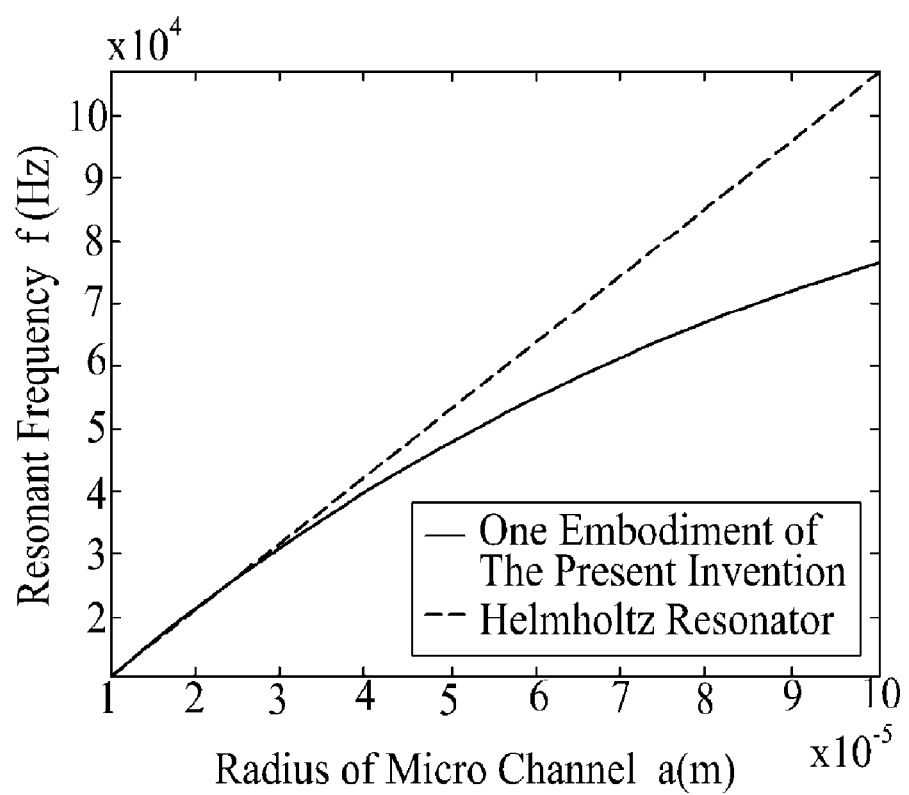
FIG. 5 is a graph comparing the difference of results between the calculation method of the Helmholtz resonator when ka<<1 and the calculation method according to one embodiment of the present invention disregarding the value of ka.

FIG. 5 is a graph comparing the difference of results between the case where ka<<1 for the Helmholtz resonator and the method that can be applied to one embodiment of the present invention disregarding the value of ka.

When the calculation method of one embodiment of the present invention holds a small radius (a) of the micro channel 140 so that the resonant frequency (f) of the system is low, and satisfies the conditions of ka<<1, the Helmholtz resonator calculation method is approached, while, on the other hand, when the radius (a) of the micro channel 140 becomes greater and the resonant frequency increases, and the assumption of the Helmholtz resonator calculation method, ka<<1, does not meet the conditions, the calculation method following the embodiment of the present invention should be applied.

Figure 6:
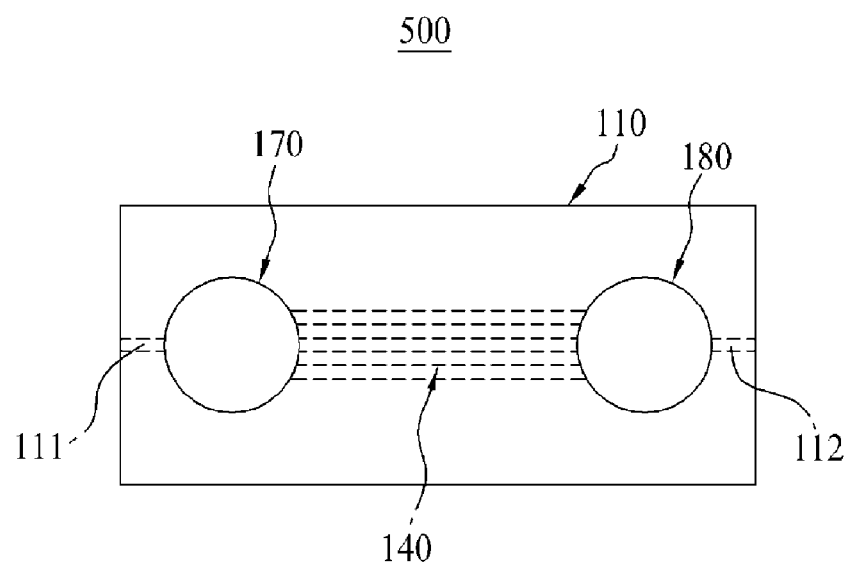
FIG. 6 is a cross-sectional view of the second embodiment of the present invention illustrating a micro viscometer.

FIG. 6 is a cross-sectional view of the second embodiment of the present invention illustrating a micro viscometer.

A micro viscometer 500 according to the second embodiment is structurally similar to the first embodiment of a micro viscometer with several differences. Therefore, identical reference numerals are used for identical composition factors and explanations are not repeated.

Referring to FIG. 6, the second embodiment of a micro viscometer 500 comprises multiple micro channels 140 on the body 110. Each micro channel 140 may have different lengths. Or, the lengths are identical so that an acoustic pressure with the same phase angle and amplitude transfers from each micro channel 140 and the sensing part 180 senses the acoustic pressure.

Figure 7:
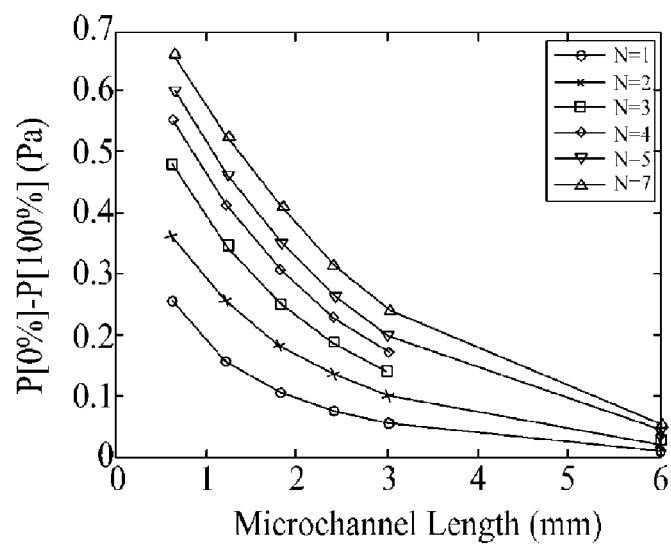
FIG. 7 is a graph of the absolute difference of acoustic pressure according to the number of micro channels when the viscosity of the fluid changes, based on the first embodiment and second embodiment of the present invention.
Figure 8:
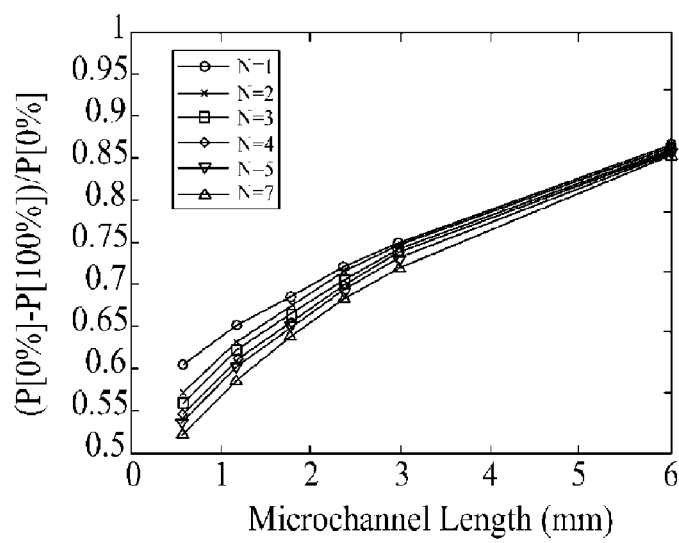
FIG. 8 is a graph of the variation rate of acoustic pressure according to the number of micro channels in identical conditions with FIG. 7.

FIG. 7 is a graph of the absolute difference of acoustic pressure according to the number of micro channels when the viscosity of the fluid changes, based on the first embodiment and second embodiment of the present invention. FIG. 8 is a graph of the variation rate of acoustic pressure according to the number of micro channels in identical conditions with FIG. 7.

As it is shown from FIG. 7 and FIG. 8, when multiple micro channels are formed within the body of a micro viscometer, the variance of the acoustic pressure decreases compared to when a single micro channel is formed within the body interior, however, the acoustic pressure increases.

For example, when the micro channel length is 3 mm in FIG. 7, and when the numbers of micro channels are 1 and 7 respectively, the acoustic absolute variance correspondingly turns out to be 0.05 Pa and 0.25 Pa. However, when checking the variance of acoustic pressure in FIG. 8 where the numbers of micro channels are 1 and 7 respectively, the acoustic pressure shows similar values of 0.75 and 0.72 correspondingly.

Thus, measurements can be more greatly made for the signal of the acoustic pressure compared to the surrounding noise when measuring the acoustic pressure at the sensing part due to the effect that a greater degree of acoustic pressure is transferred as the number of micro channels increase.

Meanwhile, it is desirable for the first thin film and second thin film to have identical resonant frequencies to increase the accuracy compared to when measuring the viscosity of the fluid in an embodiment of the present invention that deal with a micro viscometer.

Furthermore, in order to accurately measure the viscosity of the fluid even more, the spatial structure of the chamber that forms the body interior must be designed more acoustically. For this, FIG. 9 and FIG. 10 are referenced to explain this matter.

Figure 9:
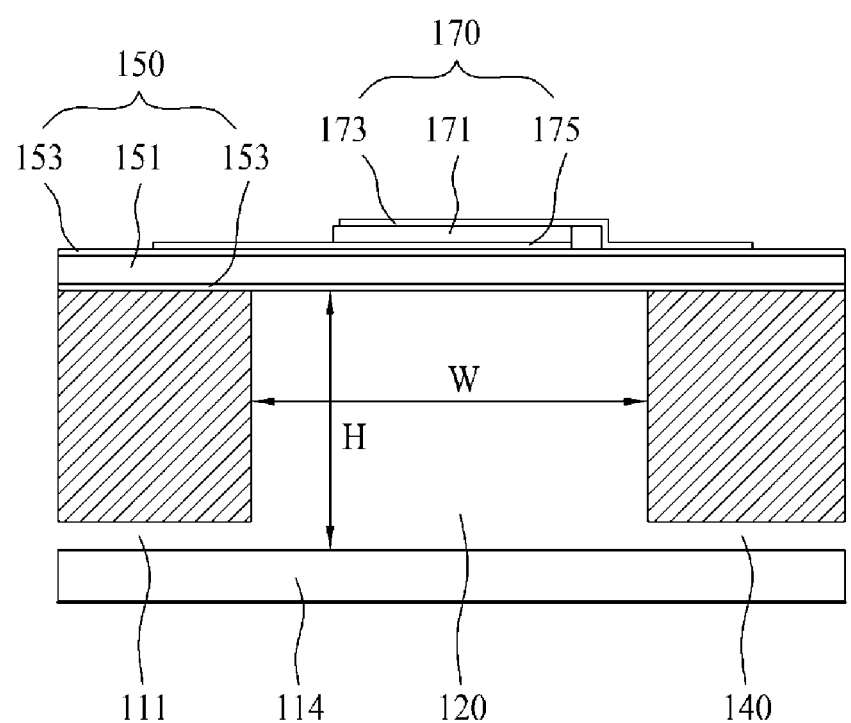
FIG. 9 is a diagrammatic view of the chamber structure of a micro viscometer according to one embodiment of the present invention.

FIG. 9 is a diagrammatic view of the chamber structure of a micro viscometer according to one embodiment of the present invention and FIGS. 10a-10b are diagrammatic views of the first resonant frequency and second resonant frequency that are transferred within the chamber of a micro viscometer, respectively.

Figure 10:
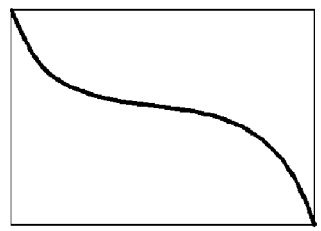
FIGS. 10a-10b are diagrammatic views of the first resonant frequency and second resonant frequency that are transferred within the chamber of a micro viscometer, respectively.
Figure 10:
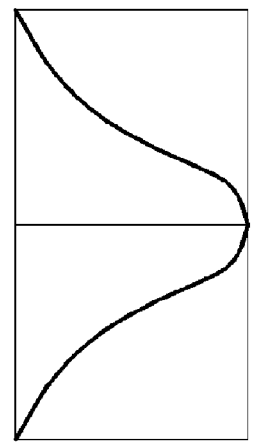

Referring to FIG. 9 and FIG. 10, the viscosity of the fluid within the body can be accurately measured by the increase in the damping effect of the acoustic pressure, which is transferred through the first chamber 120, within the micro channel 140 when the first resonant frequency that occurs from the thin film 150 transfers acoustic pressure to the first chamber 120.

Namely, in order to transfer with the greatest degree of acoustic pressure transferred to the first chamber 120 through the micro channel, the first resonance (a) must occur in the height direction of the first chamber 120. Therefore, it is necessary for the height (H) of the first chamber 120 to at least actually form a half wavelength that responds to the first resonant frequency and the width of the first chamber 120 should be shorter than the height of the first chamber 120 or the half wavelength that corresponds to the first resonant frequency.

If the width of the first chamber 120 is longer than the height (H) of the chamber or the half wavelength corresponding to the first resonant frequency, first resonance (a) occurs in the width direction of the first chamber 120 so that desirable acoustic pressure is not actually transferred through the micro channel 140. Like this, the height (H) and width (W) of the first chamber 120 depend on the first resonant frequency of the thin film 150.

Furthermore, to make manufacturing process conditions simple in building one embodiment of the present invention according to a micro viscometer, the height (H) of the first chamber 120 should have an equal wavelength corresponding to the frequency in accordance with a second resonant (b) of the thin film 150.

The width (W) of the first chamber 120 should be at least smaller than the half wavelength of the second resonant frequency. This is because when the second resonant frequency is larger than the length of the half wavelength, the first resonant frequency of the thin film 150 with high degree of the acoustic pressure in the width direction of the first chamber 120 occurs which makes it actually hard for the acoustic pressure transfer in the height direction of the first chamber that is the wavelength direction of progress.

The structure of the chamber as above is not shown. However, it can identically used not only for the first chamber 120 of the actuating part but also the second chamber 130 of the sensing part.

Meanwhile, to measure the viscosity of the fluid more accurately it is necessary to cancel the noise occurring due to the electric effect between the actuating part 170 and the sensing part 180 when a micro viscometer operates.

Figure 11:
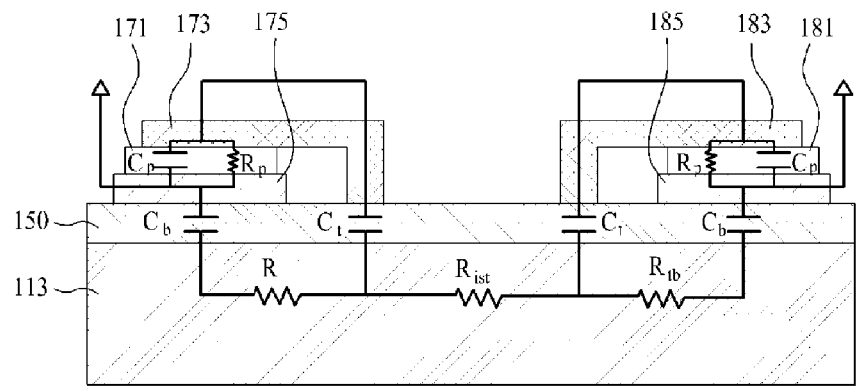
FIG. 11 is the electric circuit of a micro viscometer according to one embodiment of the present invention.

FIG. 11 is the electric circuit of a micro viscometer according to one embodiment of the present invention.

As illustrated, a micro viscometer constructs the electric circuit by dividing into the actuating part and sensing part. When applying voltage in the actuating part at this moment the current following the voltage actually should not flow into sensing part so that the viscosity of the fluid can be derived from the genuine acoustic pressure.

Due to the characteristics of the substrate 113, when the voltage applied to the actuating part is a direct current signal the electric impedance becomes infinite so that the current following the applied voltage of the actuating part does not flow into the sensing part, however, when the voltage applied on the actuating part is a alternating current the impedance becomes lower which brings the resistance of the substrate to decrease.

The current following the voltage, which is applied on the actuating part, flows into the sensing part which causes inaccurate measurements of viscosity of fluids due to an electrical noise included in the acoustic pressure measurement of the sensing part.

Figure 12:
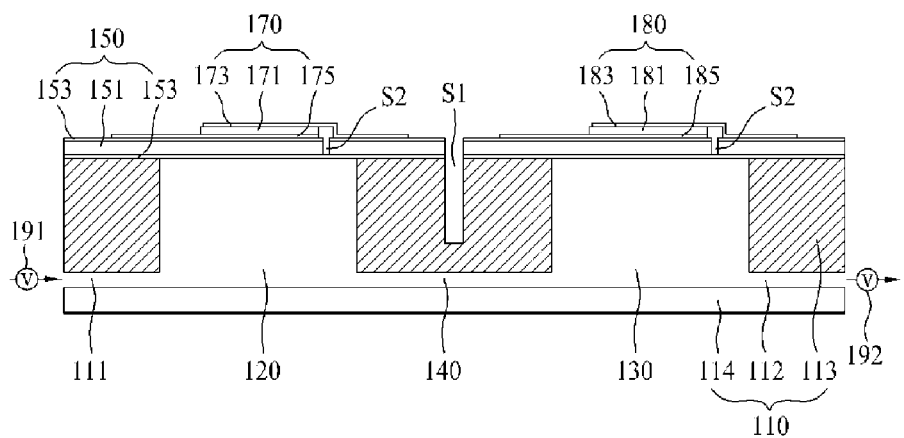
FIG. 12 is the trench structure of a micro viscometer according to one embodiment of the present invention.

Therefore, as shown in FIG. 12, in a micro viscometer according to one embodiment of the present invention, electrical separation of the actuating part 170 from the sensing part 180 is necessary.

Physically, a thin film 150 has a trench S1 formed between the first chamber 120 and second chamber 130 so that the actuating part 170 and sensing part 180 actually has electrical separation, and the main trench (S1) extends to a portion of the substrate 113 positioned on the thin film bottom. The number of main trench (S1) can be at least one.

Preferably, the main trench (S1) is formed on the substrate 113 and cuts through the thin film 150 and has a depth of more than ½ of the thickness of the substrate 113.

When applying voltage on the actuating part 170 or sensing part 180, noise can be measured with the measurement of the viscosity of fluid from acoustic pressure from the effect of the applied current in between the first electrode 175 and second electrode 173 of the actuating part 170 or in between the third electrode 185 and fourth electrode 183 of the sensing part 180.

To prevent this, the thin film should provide electrical separation between the first electrode 175 and second electrode 173 or between the third electrode 185 and fourth electrode 183. In one embodiment, a supporting (or auxiliary) trench (S2) can be constructed for electrical separation between the first electrode 175 and second electrode 173 or between the third electrode 185 and fourth electrode 183 of the thin film 150.

Like this, a micro viscometer according to one embodiment of the present invention, enables the measurement of viscosity not only in liquid but also gas, and since the size of this viscometer holds its merits by being itself the smallest model, not only does it become used as an independent equipment exclusively for viscosity but also allows accurate viscosity measurement of the fluid when included as a component of another equipment.

Furthermore, as the interest on the bio technology has risen, the application has become various, in measurements for such as viscosity for various fluids within the living body, including the viscosity measurement on blood and viscosity and variance measurement of amplified DNA due to Micro PCR, etc.

In addition, this present invention, regarding a micro viscometer, can measure the viscosity and variance with only a minimal amount of fluid by utilizing MEMS (Micro-Electro Mechanical Systems) structure so that measuring hardly obtainable or high cost reagents or gas is possible. Also, due to the fact that gravity does not affect the device the viscometer can disregard the location or direction of placement. Furthermore, the viscometer quickly and efficiently measures the viscosity with a character of small size that promotes the use as an independent device and also does not take much space as a component of another device.

As the present invention may be embodied in several forms without departing from the spirit or essential characteristics thereof, it should also be understood that the above-described examples are not limited by any of the details of the foregoing description, unless otherwise specified, but rather should be construed broadly within its spirit and scope as defined in the appended claims, and therefore all changes and modifications that fall within the meets and bounds of the claims, or equivalences of such meets and bounds are therefore intended to be embraced by the appended claims.

What is claimed is:

1. A micro viscometer, comprising:
   a first chamber and a second chamber spatially separated from the first chamber by an interval;
   a micro channel for fluid communication between the first chamber and the second chamber; and
   a first thin film and a second thin film disposed on the first chamber and the second chamber, respectively,
   wherein a height of the first chamber is substantially same as a half wavelength corresponding to a first resonant frequency of the first thin film and a width of the first chamber is narrower than the height of the first chamber and
   wherein a height of the second chamber is substantially same as a half wavelength corresponding to a second resonant frequency of the second thin film and a width of the second chamber is narrower than the height of the second chamber.

2. The micro viscometer of claim 1,
   wherein the first resonant frequency is substantially identical to the second resonant frequency.

3. The micro viscometer of claim 1,
wherein the first thin film and the second thin film each include a silicon wafer and an insulator disposed on top and bottom surfaces of the silicon wafer.

4. The micro viscometer of claim 3,
wherein the insulator comprises a Si type layer.

5. The micro viscometer of claim 1,
wherein at least one side of the first chamber, the second chamber and the micro channel is coated with a hydrophilic layer.

6. The micro viscometer of claim 1,
wherein a volume of the first chamber is substantially identical to a volume of the second chamber.

7. A micro viscometer, comprising:
a first chamber and a second chamber separated from the first chamber by an interval;
a micro channel for fluid communication between the first chamber and the second chamber; and
a first thin film and a second thin film disposed on the first chamber and the second chamber, respectively,
wherein a height of the first chamber is substantially same as a wavelength corresponding to a first resonant frequency of the first thin film and a width of the first chamber is narrower than the height of the first chamber and
wherein a height of the second chamber is substantially same as a wavelength corresponding to a second resonant frequency of the second thin film and a width of the second chamber is narrower than the height of the second chamber.

8. The micro viscometer of claim 7,
wherein the first resonant frequency is substantially identical to the second resonant frequency.

9. The micro viscometer of claim 7,
wherein the first thin film and the second thin film each include a silicon wafer and an insulator disposed on top and bottom surfaces of the silicon wafer.

10. The micro viscometer of claim 9,
wherein the insulator comprises a Si type layer.

11. The micro viscometer of claim 7,
wherein at least one side of the first chamber, the second chamber and the micro channel is coated with a hydrophilic layer.

12. The micro viscometer of claim 7,
wherein a volume of the first chamber is substantially identical to a volume of the second chamber.

* * * * *